(12) United States Patent
Merchav et al.

(10) Patent No.: US 6,911,201 B1
(45) Date of Patent: Jun. 28, 2005

(54) METHOD OF PRODUCING UNDIFFERENTIATED HEMOPOIETIC STEM CELLS USING A STATIONARY PHASE PLUG-FLOW BIOREACTOR

(75) Inventors: Shoshana Merchav, Haifa (IL); Shai Meretzki, Nesher (IL)

(73) Assignee: Technion Research & Development Foundation Ltd., Haifa (IL)

( * ) Notice: Subject to any disclaimer, the term of this patent is extended or adjusted under 35 U.S.C. 154(b) by 0 days.

(21) Appl. No.: 09/890,401

(22) PCT Filed: Feb. 4, 2000

(86) PCT No.: PCT/US00/02688

§ 371 (c)(1),
(2), (4) Date: Jul. 31, 2001

(87) PCT Pub. No.: WO00/46349

PCT Pub. Date: Aug. 10, 2000

Related U.S. Application Data (60) Provisional application No. 60/118,789, filed on Feb. 4, 1999.

(51) Int. Cl.[7] .............................. C12N 5/06; C12N 5/08; C12N 11/08; C12M 3/00; A61F 2/00
(52) U.S. Cl. ...................... 424/93.7; 424/423; 435/177; 435/180; 435/347; 435/373; 435/395; 435/398; 435/289.1
(58) Field of Search ................................ 424/93.7, 423; 435/177, 180, 347, 373, 395, 398, 289.1

(56) References Cited

U.S. PATENT DOCUMENTS

| | | | |
|---|---|---|---|
| 5,266,476 A | 11/1993 | Sussman et al. ............ | 435/399 |
| 5,437,994 A | 8/1995 | Emerson et al. ............ | 435/373 |
| 5,510,262 A | 4/1996 | Stephanopoulos et al. .. | 435/403 |
| 5,541,107 A | 7/1996 | Naughton et al. ............ | 435/29 |

OTHER PUBLICATIONS

Kadouri et al, "Dynamic Changes in Cytokine Secretion by Stromal Cells During Prolonged Maintenance Under Protein–Free Conditions", *Intl. J. Cell Cloning*, 10(5):299–308, 1992.

Rosenzweig et al, "Enhanced Maintenance and Retroviral Transduction of Primitive Hematooietic Progenitor Cells Using a Novel Three–Dimensional Culture System", *Gene Therapy*, 4:928–936, 1997.

Kadouri, A., "Cultivation of Anchorage–Dependent Mammalian Cells and Production of Various Metabolites", *Colloids and Surfaces B: Biointerfaces*, 2:265–272, 1994.

Otsuka et al, "Expression of the *c–kit* Ligand and Interleukin 6 Genes in Mouse Bone Marrow Stromal Cell Line", 12(4):409–415, 1994.

*Primary Examiner*—David M. Naff
(74) *Attorney, Agent, or Firm*—G.E. Ehrlich (1995) Ltd.

(57) ABSTRACT

A method of expanding/maintaining undifferentiated hemopoietic stem cells or progenitor cells by obtaining undifferentiated hemopoietic stem cells or progenitor cells; and either seeding the undifferentiated hemopoietic stem cells or progenitor cells into a stationary phase plug-flow bioreactor in which a three-dimensional stromal cell culture has been pre-established on a substrate in the form of a sheet, the substrate including a non-woven fibrous matrix forming a physiologically acceptable three-dimensional network of fibers, thereby expanding/maintaining undifferentiated hemopoietic stem cells or progenitor cells, or culturing the undifferentiated hemopoietic stem cells or progenitor cells in conditioned medium obtained from such a reactor.

40 Claims, 4 Drawing Sheets

METHOD OF PRODUCING UNDIFFERENTIATED HEMOPOIETIC STEM CELLS USING A STATIONARY PHASE PLUG-FLOW BIOREACTOR

This application claims the benefit of provisional application No. 60/118,789 filed Feb. 4, 1999.

FIELD AND BACKGROUND OF THE INVENTION

The present invention relates to a method and apparatus for maintenance and expansion of hemopoietic stem cells. More particularly, the present invention relates to a three dimensional stromal cell plug flow bioreactor for the maintenance and/or expansion of hemopoietic stem cells and/or for the production of a conditioned medium for the maintenance and/or expansion of hemopoietic stem cells.

The hemopoietic system in mammals is composed of a heterogenous population of cells that range in function from mature cells with limited proliferative potential to pluripotent stem cells with extensive proliferative, differentiative and self renewal capacities (1–3). Hemopoietic stem cells (HSC) are exclusively required for hemopoietic reconstitution following transplantation and serve as a primary target for gene therapy. In spite of the key role of stem cells in maintaining the hemopoietic system, their extremely low frequency in hemopoietic tissue, as well as the limited ability to maintain or expand undifferentiated stem cells under ex-vivo conditions for prolonged periods of time, not only remains a major drawback to essential clinical applications of these cells, but also reflects the current unavailability of, and the need for, novel stem cell regulators.

It is widely accepted that stem cells are intimately associated in vivo with discrete niches within the marrow (4–6), which provide molecular signals that collectively mediate their differentiation and self renewal, via cell-cell contacts or short-range interactions (7). These niches are part of the "hemopoietic inductive microenvironment" (HIM), composed of marrow stromal cells, e.g., macrophages, fibroblasts, adipocytes and endothelial cells (8). Marrow stromal cells maintain the functional integrity of the HIM by providing extracellular matrix (ECM) proteins and basement membrane components that facilitate cell-cell contact (9–11). They also provide various soluble or resident cytokines needed for controlled hemopoietic cell differentiation and proliferation (12–14).

In view of the above, it is not surprising that efforts to develop culture systems for the prolonged maintenance of human HSC were mainly focused on the use of pre-established primary marrow stromal cell monolayers. These included long-term cultures of unirradiated (Dexter cultures, 15) or irradiated (16–19) primary human marrow stroma, as well as human or murine stromal cell lines (16, 19–24), with or without exogenously added cytokines. Output assays for HSC initially relied on the capacity of such cells to produce myeloid progeny (long-term culture initiating cells; LTC-IC) or to generate colonies with cobblestone morphology (cobblestone area forming cells; CAFC) after prolonged culture (5–7 Weeks) on such stromal cells (16,17). In spite of the widespread use of LTC-IC and CAFC assays, it is becoming increasingly obvious, however, that they detect highly primitive progenitors, rather than true repopulating hemopoietic stem cells (25, 26).

A recently developed human stem cell assay detects a SCID repopulating cell (SRC), which homes to the bone marrow of non-obese diabetic (NOD)/SCID mice (27), where it gives rise to human myeloid, lymphoid, erythroid and CD34+ progenitor populations (28–30). The SRC is exclusively found in hemopoietic cell fractions expressing the CD34+38− surface antigen (31) and its frequency in CB ($\frac{1}{3} \times 10^5$ cells) is enriched as compared to BM ($\frac{1}{6} \times 10^5$ cells) or mobilized PB ($\frac{1}{6} \times 10^6$ cells) (32). Very recent studies showed that the SRC resides within a subpopulation of CD34+/38−/CXCR4+ cells (33). CXCR4, a surface receptor for the chemokine stromal cell-derived factor 1 (SDF-1, 34), is apparently essential for homing and engraftment of human hemopoietic stem cells in the NOD/SCID marrow (33).

Studies aimed at inducing prolonged maintenance/expansion of human HSC on stromal cell cultures were mainly based on CAFC, LTC-IC or the CD34+38− phenotype as end-point assays (16, 19–24). Rare reports of SRC maintenance/expansion in stromal cell cultures fail to indicate significant long-term support. For example, allogeneic human marrow stroma was found to induce short-term (7-day) SRC maintenance, followed by a rapid, marked decline (6-fold) in activity (26). The inability to support the long-term maintenance/expansion of transplantable human stem cells on stromal cell layers, may be attributed to several factors related to in vitro cultures of these cells. Among these, one may include the use of stromal cell monolayers, which do not reflect the in vivo growth conditions within the natural, three-dimensional structure of the bone marrow. Such conditions may diminish the capacity of stromal cells to provide the optimal, appropriate supportive microenvironment, as well as the capacity of stem cells to localize in specific niches and to physically interact with stromal cells and their products. Indeed, evidence for the importance of a three dimensional (3D) structure for the biological activity of hemopoietic progenitor cells, is provided by the superior growth of a human hemopoietic cell line on stromal cells seeded in a 3D collagen matrix, as compared to their proliferation on monolayers of such cells (35). More importantly, a 3D tantalum-coated porous biomaterial, was recently shown to enhance the short-term maintenance of macaque LTCIC or CD34+38− cells, as compared to cells cultured alone or on marrow stromal cell monolayers (36). The effect of stromal cell-coated 3D carriers, was, however, not investigated.

Recent studies have shown the murine AFT024 cell line to be superior than human stroma, in supporting 2–3 week survival and maintenance (albeit not expansion) of human CB SRC (37). This line has been found to express several novel HIM genes encoding membrane-bound proteins (21, 38, 39), which may have an essential role in stem cell physiology. The possible expression of these and other genes by stromal cells under conditions which more closely mimic their 3D marrow microenvironment, and thus enable their optimal, physiological functional activity, has yet to be determined.

Extensive studies have shown that stroma non-contact cultures (19, 21, 22, 40, 41) or stroma conditioned media (SCM) (21, 42–44), alone or with cytokines, can support the ex-vivo maintenance or expansion of primitive hemopoietic progenitors. SCM has also been shown to improve the recovery and transduction efficiency of such cells (45, 46). While these findings again stress the importance of soluble stromal cell factors, the use of LTC-IC, CAFC or CD34+38− end-points in such assays cannot reflect the effect of SCM on maintenance/expansion of transplantable HSC. Furthermore, it is not known whether such SCM, obtained from monolayer cultures of stromal cells, indeed contains all stromal cell-associated gene products involved in human HSC physiology.

Recent attention aimed at ex-vivo expansion of transplantable hemopoietic stem cells has focused on the establishment of cytokine-supplemented suspension cultures (47–53). These studies have helped identify the major relevant cytokines for this process, e.g., early-acting ones such as stem cell factor (SCF), FLT3 ligand and thrombopoietin (TPO). Nevertheless, variable results have been obtained, indicating short-term loss (48, 49), maintenance (50–52) but also some rare examples of SRC expansion, following during 2–4 weeks of culture (47, 53). The interactive capacity of these cytokines and stromal cells, under 3D growth conditions, to support the maintenance/expansion of SRC, has not yet been defined.

There is thus a widely recognized need for, and it would be highly advantageous to have, a method and apparatus for ex-vivo expansion and/or maintenance of transplantable hemopoietic stem cells devoid of the above limitations, with superior results as is compared to the teachings of the prior art.

SUMMARY OF THE INVENTION

While reducing the present invention to practice, a plug flow bioreactor system which closely mimics the 3D bone marrow microenvironment and which is capable of supporting the growth and prolonged maintenance of stromal cells, has been developed. The latter were seeded on porrosive inorganic carriers made of a non woven fabric matrix of polyester (54), enabling the propagation of large cell numbers in a relatively small volume. The structure and packing of the carrier have a major impact on oxygen and nutrient transfer, as well as on local concentrations and released stromal cell. products (e.g., ECM proteins, cytokines, 55). In addition, the capacity of stromal cells cultured in this system to promote the maintenance/expansion of transplantable human hemopoietic stem cells via direct cell-cell contact has been determined to be far superior over prior art methods. Furthermore, the capacity of conditioned medium of stromal cells cultured in this system to promote the maintenance/expansion of transplantable human hemopoietic stem cells via novel stromal-cell associated stem cell factors included therein, has been determined to be far superior over prior art methods.

Thus, according to one aspect of the present invention there is provided a method of expanding/maintaining undifferentiated hemopoietic stem cells or progenitor cells, the method comprising the steps of (a) obtaining undifferentiated hemopoietic stem cells or progenitor cells; and (b) seeding the undifferentiated hemopoietic stem cells or progenitor cells into a stationary phase plug-flow bioreactor in which a three dimensional stromal cell culture has been pre-established on a substrate in the form of a sheet, the substrate including a non-woven fibrous matrix forming a physiologically acceptable three-dimensional network of fibers, thereby expanding/maintaining undifferentiated hemopoietic stem cells or progenitor cells.

According to still further features in the described preferred embodiments the method further comprising the step of isolating the undifferentiated hemopoietic stem cells or progenitor cells.

According to another aspect of the present invention there is. provided a method of expanding/maintaining undifferentiated hemopoietic stem cells or progenitor cells, the method comprising the steps of (a) obtaining undifferentiated hemopoietic stem cells or progenitor cells; and (b) culturing the undifferentiated hemopoietic stem cells or progenitor cells in a medium containing a stromal cell conditioned medium, the stromal cell conditioned medium being derived from a stationary phase plug-flow bioreactor in which a three dimensional stromal cell culture has been established on a substrate in the form of a sheet, the substrate including a non-woven fibrous matrix forming a physiologically acceptable three-dimensional network of fibers, thereby expanding/maintaining undifferentiated hemopoietic stem cells or progenitor cells.

According to yet another aspect of the present invention there is provided a method of preparing a stromal cell conditioned medium useful in expanding/maintaining undifferentiated hemopoietic stem cells or progenitor cells, the method comprising the steps of (a) establishing a stromal cell culture in a stationary phase plug-flow bioreactor on a substrate in the form of a sheet, the substrate including a non-woven fibrous matrix forming a physiologically acceptable three-dimensional network of fibers, thereby expanding/maintaining undifferentiated hemopoietic stem cells or progenitor cells; and (b) when a desired stromal cell density has been achieved, collecting medium from the stationary phase plug-flow bioreactor, thereby obtaining the stromal cell conditioned medium useful in expanding/maintaining undifferentiated hemopoietic stem cells or progenitor cells.

According to still another aspect of the present invention there is provided a method of transplanting undifferentiated hemopoietic stem cells or progenitor cells into a recipient, the method comprising the steps of (a) expanding/maintaining the undifferentiated hemopoietic stem cells or progenitor cells by (i) obtaining undifferentiated hemopoietic stem cells or progenitor cells; and (ii) seeding the undifferentiated hemopoietic stem cells or progenitor cells into a stationary phase plug-flow bioreactor in which a three dimensional stromal cell culture has been pre-established on a substrate in the form of a sheet, the substrate including a non-woven fibrous matrix forming a physiologically acceptable three-dimensional network of fibers, thereby expanding/maintaining undifferentiated hemopoietic stem cells or progenitor cells; and (b) transplanting the undifferentiated hemopoietic stem cells or progenitor cells resulting from step (a) in the recipient.

According to still further features in the described preferred embodiments the method further comprising the step of isolating the undifferentiated hemopoietic stem cells or progenitor cells prior to step (b).

According to an additional aspect of the present invention there is provided a method of transplanting undifferentiated hemopoietic stem cells or progenitor cells into a recipient, the method comprising the steps of (a) expanding/maintaining the undifferentiated hemopoietic stem cells or progenitor cells by (i) obtaining undifferentiated hemopoietic stem cells or progenitor cells; and (ii) culturing the undifferentiated hemopoietic stem cells or progenitor cells in a medium containing a stromal cell conditioned medium, the stromal cell conditioned medium being derived from a stationary phase plug-flow bioreactor in which a three dimensional stromal cell culture has been established on a substrate in the form of a sheet, the substrate including a non-woven fibrous matrix forming a physiologically acceptable three-dimensional network of fibers, thereby expanding/maintaining undifferentiated hemopoietic stem cells or progenitor cells.

According to yet an additional aspect of the present invention there is provided a bioreactor plug comprising a container having an outlet and an inlet and containing therein a substrate in the form of a sheet, the substrate including a non-woven fibrous matrix forming a physiologically acceptable three-dimensional network of fibers, the substrate supporting at least $5 \times 10^6$ stromal cells per cubic centimeter of the substrate.

According to still an additional aspect of the present invention there is provided a plug-flow bioreactor comprising the above bioreactor plug.

According to further features in preferred embodiments of the invention described below, the undifferentiated hemopoietic stem cells or progenitor cells are cells isolated from a tissue selected from the group consisting of cord blood, mobilized peripheral blood and bone-marrow.

According to still further features in the described preferred embodiments the undifferentiated hemopoietic stem cells or progenitor cells and stromal cells of the stromal cell culture share common HLA antigens.

According to still further features in the described preferred embodiments the undifferentiated hemopoietic stem cells or progenitor cells and stromal cells of the stromal cell culture are from a single individual.

According to still further features in the described preferred embodiments the undifferentiated hemopoietic stem cells or progenitor cells and stromal cells of the stromal cell culture are from different individuals.

According to still further features in the described preferred embodiments the undifferentiated hemopoietic stem cells or progenitor cells and stromal cells of the stromal cell culture are from the same species.

According to still further features in the described preferred embodiments the undifferentiated hemopoietic stem cells or progenitor cells and stromal cells of the stromal cell culture are from different species.

According to still further features in the described preferred embodiments stromal cells of the stromal cell culture are grown to a density of at least $5 \times 10^6$ cells per a cubic centimeter of the substrate.

According to still further features in the described preferred embodiments stromal cells of the stromal cell culture are grown to a density of at least $10^7$ cells per a cubic centimeter of the substrate.

According to still further features in the described preferred embodiments the step of seeding the undifferentiated hemopoietic stem cells or progenitor cells into the stationary phase plug-flow bioreactor is effected while flow in the bioreactor is shut off for at least 10 hours following the seeding.

According to still further features in the described preferred embodiments the fibers form a pore volume as a percentage of total volume of from 40 to 95% and a pore size of from 10 microns to 100 microns.

According to still further features in the described preferred embodiments the matrix is made of fiber selected from the group consisting of flat, non-round, and hollow fibers and mixtures thereof, the fibers being of from 0.5 microns to 50 microns in diameter or width.

According to still further features in the described preferred embodiments the matrix is composed of ribbon formed fibers having a width of from 2 microns According to still further features in the described preferred embodiments the ratio of width to thickness of the fibers is at least 2:1.

According to still further features in the described preferred embodiments the matrix having a pore volume as a percentage of total volume of from 60 to 95%.

According to still further features in the described preferred embodiments the matrix has a height of 50–1000 $\mu$m.

According to still further features in the described preferred embodiments the material of the matrix is selected from the group consisting of polyesters, polyalkylenes, polyfluorochloroethylenes, polyvinyl chloride, polystyrene, polysulfones, cellulose acetate, glass fibers, and inert metal fibers.

According to still further features in the described preferred embodiments the matrix is in a shape selected from the group consisting of squares, rings, discs, and cruciforms.

According to still further features in the described preferred embodiments the matrix is coated with poly-D-lysine.

The present invention successfully addresses the shortcomings of the presently known configurations by providing more effective means for expanding/maintaining undifferentiated hemopoietic stem cells. Implementation of the method and bioreactor of the present invention may involve performing or completing selected tasks or steps manually, automatically, or a combination thereof. Moreover, according to actual instrumentation and equipment of preferred embodiments of the method and bioreactor of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and bioreactor of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings is making apparent to those skilled in the art how the several forms of the invention may be embodied in practice.

In the drawings.

DESCRIPTION OF THE PREFERRED EMBODIMENTS

The present invention is of methods and bioreactor for hemopoietic stem cell expansion/maintenance which can be used for transplantation in a recipient or for other purposes as if further detailed hereinunder. Specifically, the present invention is of a three dimensional stromal cell plug flow bioreactor for the maintenance and/or expansion of t o hemopoietic stem cells and/or for the production of a conditioned medium for the maintenance and/or expansion of hemopoietic stem cells, which can be used in a variety of applications.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Current strategies aimed at long-term ex-vivo maintenance or expansion of transplantable human hemopoietic stem cells (HSC), have so far been met with limited success. A novel three dimensional (3D) plug flow bioreactor which closely mimics the bone marrow microenvironment and which is capable of supporting the growth and prolonged maintenance of marrow stromal cells is described herein. The latter are seeded on porrosive carriers made of a non woven fabric matrix of polyester, packed in a glass column, thereby enabling the propagation of large cell numbers in a relatively small volume. In the examples provided in the Example section that follows, the bioreactor was seeded with the murine 14F1.1 stromal cell line or alternatively with primary human marrow stromal cells. By day 40 following seeding, the carriers contained a 100-fold increased cell density. The density at various levels of the column was the same, indicating a homogenous transfer of oxygen and nutrients to the cells. Media conditioned by stromal cells within the bioreactor (3D SCM) was superior to stromal cell monolayer (2D) SCM, in supporting the long-term maintenance of human cord blood (CB) CD34+38− cells. 3D SCM was also capable of supporting the expansion of CD34+38− CXCR4+ cells, which represent SCID/NOD repopulating cells (SRC). In the presence of cytokines (FLT3 ligand and TPO), 3D SCM enhanced stem cell self renewal and inhibited differentiation, while the opposite effect was induced by 2D SCM+cytokines. Three dimensional stromal-stem cell cocultures also exhibited superior maintenance of CD34+ 38− cells than cocultures on monolayer stromal cells. These findings demonstrate that the 3D plug flow bioreactor provides a suitable system for ex-vivo maintenance/expansion of human HSC via superior stromal-stem cell contact and perhaps via stromal cell production of known and/or novel stem cell regulators.

The human HSC is an essential target for transplantation and gene therapy. The highly reduced frequency of HSCs, as well as the current unavailablity of growth factors capable of inducing stem cell self renewal in the absence of terminal differentiation, still provide a major hindrance to the implementation of such strategies, well as to the large-scale setup of HSC "banks".

Current strategies aimed at long-term maintenance/ expansion of undifferentiated human HSC, have so far been met with limited success. While recent studies with cytokine-supplemented suspension cultures have shown some SRC expansion, this process was also accompanied by a massive increment of early hemopoietic progenitors (53, 62), indicating that a substantial degree of stem cell differentiation was taking place. An ideal system would be one, for example, in which SRC were expanded, while LTC-IC remain reduced in numbers.

Figure 6A:
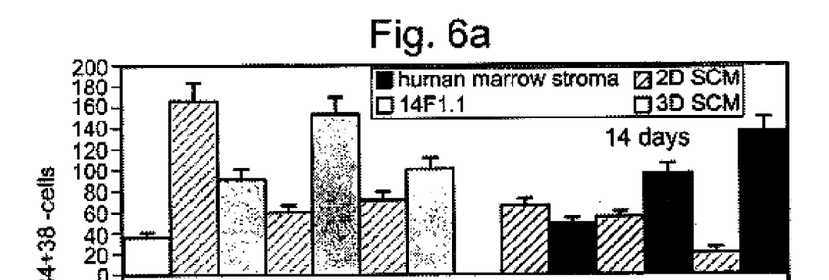
FIGS. 6a–b demonstrate the effect of 3D versus 2D 14F1.1 conditioned medium on CD34+38− expansion. CD34+ cells were seeded in suspension cultures in the presence of various concentrations of conditioned medium from 14F1.1 and primary human marrow stroma. CD34+38− cell numbers were determined by FACS analysis. Results represent the mean ±SD of 2 independent experiments.
Figure 6B:
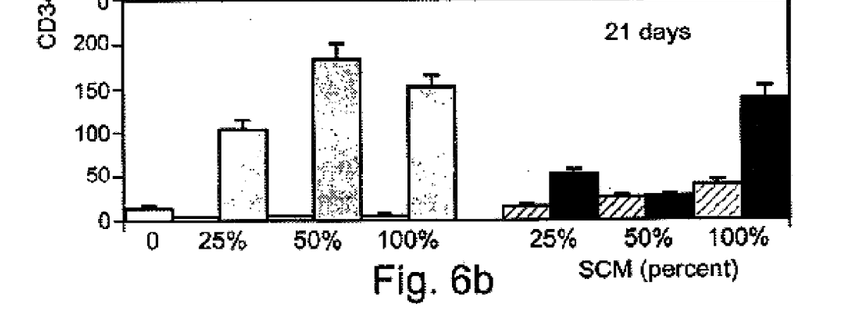

Current systems for hemopoietic cell expansion employ perfused suspension cultures of hemopoietic cells, alone (see, U.S. Pat. No. 5,646,043) or seeded on stromal-cell monolayers (see, U.S. Pat. No. 5,605,822). While the former system demonstrates a tremendous production of committed progenitors, the latter suffers from the non-physiological nature of monolayer stromal-stem cell interactions. Additional systems for stem cell expansion describe the use of stromal cell conditioned media (U.S. Pat. Nos. 4,536,151 and 5,437,994). However, the latter were obtained from stromal cell monolayer cultures, which are clearly shown herein to be inferior and different in stem cell activating capacity, as compared to 3D SCM (see, Table 3 of the Examples section). Although a stationary phase bioreactor using stromal cell-coated glass beads has recently been described (U.S. Pat. No. 5,906,940), the beads do not provide a physiological, 3D structure and allow the propagation of a 10-fold lower number of stromal cells per ml, as compared to the carriers employed while reducing the present invention to practice. The advantage of a 3D versus monolayer stromal cell culture is clearly demonstrated by the findings presented herein of the superior capacity of 3D derived SCM or 3D stromal cell cultures to support the maintenance of CD34+38− cells (see, FIGS. 6 and 7). The superior effect of 3D SCM may be attributed to enhanced levels of known cytokines or novel stem cell regulators.

Experiments aimed at evaluating the combined effects of 3D SCM and various cytokines (SCF, FLT3 ligand, TPO), on CD34+38−CXCR4+ (or SRC) maintenance/expansion (Table 3), clearly show a beneficial effect of 3D SCM in the presence of FLT3 ligand and TPO, but not SCF. These findings can be attributed to a relative inhibitory effect of 3D SCM on stem cell differentiation. These findings strongly indicate that under 3D conditions, novel stromal cell -associated factors which, perhaps less active themselves, may act synergistically with such cytokines were produced. The use of LTC-IC and committed progenitor cell (GM-CFU) output readouts, in addition to CD34+ output, allow to test for stem cell differentiation.

The bioreactor described herein is unique in that it combines both 3D stromal cell cultures with a continuous flow system. While 3D stromal-hemopoietic cell systems without continuous medium flow have recently been described (U.S. Pat. No. 5,541,107), the findings described herein (see, for example, FIG. 7) clearly demonstrate the diminished advantage of 3D stromal cell cultures relative to monolayers, in the absence of continuous flow.

The 3D plug-flow bioreactor described herein is capable of supporting the long-term growth of stromal cell lines, as well as primary marrow stromal cells, The use of stromal cells in the bioreactor is not only essential for the establishment of superior stromal-stem cell contact (via unique "niches" and cell-cell, cell-ECM interactions), but also for stromal cell production of known and novel soluble and membrane-bound cytokines. Stromal cells can facilitate the supplementation of such bioreactors with appropriate cytokines, by using genetically engineered cytokine-producing variants.

Bioreactor stromal cells can also be engineered to serve as retroviral packaging cell lines, enabling the efficient transduction of genetic material into stem cells, within the bioreactor itself. The use of various stromal cells in the bioreactor can also allow the selection of the most suitable substrate for purging of Ph-positive stem cells, the latter known for their lesser capacity for stromal cell adherence (63). Primary stromal cells have the advantage that they enable the establishment of "autologous" stromal-stem cell bioreactors, on which autologous or even cord blood stem cells can be expanded and which eliminate the need to remove stromal cells prior to transplantation.

While the initial seeding experiments in the bioreactor indicated a rather small yield of CD34+38− cells in the carrier, the medium flow rate following seeding, as well as initial CD34+ cell numbers seeded into the bioreactor can be readily optimized. CD34+38−CXCR4+analysis at early time points (1–4 days) following seeding is essential for such optimization.

In sharp distinction to prior art methods, the bioreactor of the present invention employs a growth matrix that substantially increases the available attachment surface for the adherence of the stromal cells so as to mimic the mechanical infrastructure of bone marrow. For example, for a growth matrix of 0.5 mm in height, the increase is by a factor of at least from 5 to 30 times, calculated by projection onto a base of the growth matrix. Such an increase by a factor of about 5 to 30 times, is per unit layer, and if a plurality of such layers, either stacked or separated by spacers or the like, is used, the factor of 5 to 30 times applies per each such structure. When the matrix is used in sheet form, preferably non-woven fiber sheets, or sheets of open-pore foamed polymers, the preferred thickness of the sheet is about 50 to 1000 $\mu$m or more, there being provided adequate porosity for cell entrance, entrance of nutrients and for removal of waste products from the sheet. According to a preferred embodiment the pores having an effective diameter of 10 $\mu$m to 100 $\mu$m. Such sheets can be prepared from fibers of various thicknesses, the preferred fiber thickness or fiber diameter range being from about 0.5 $\mu$m to 20 $\mu$m, still more preferred fibers are in the range of 10 $\mu$m to 15 $\mu$m in diameter.

The structures of the invention may be supported by, or even better bonded to, a porous support sheet or screen providing for dimensional stability and physical strength.

Such matrix sheets may also be cut, punched, or shredded to provide particles with projected area of the order of about 0.2 mm$^2$ to about 10 mm$^2$, with the same order of thickness (about 50 to 1000 $\mu$m).

Further details relating to the fabrication, use and/or advantages of the growth matrix which was used to reduce the present invention to practice are described in U.S. Pat. No. 5,168,085, and in particular, U.S. Pat. No. 20 5,266,476, both are incorporated herein by reference.

As will readily be appreciated by the skilled artisan, the present invention provides expanded undifferentiated hemopoietic stem cell population which can be used in a variety of applications, such as, but not limited to: (i) expansion of human stem cells (of autologous or cord blood source) on recipient stroma, without the need for stromal-stem cell separation prior to transplantation; (ii) depletion of Ph+ CML stem cells in an autologous setting via stromal-stem cell interactions; (iii) gene transfer into self-renewing stem cells within the bioreactor or following harvesting from the bioreactor; (iv) production of 3D stromal cell conditioned medium (SCM) for ex-vivo maintenance/expansion of undifferentiated hemopoietic stem cells in suspension cultures or in a stem cell bioreactor; (v) isolation of novel proteins inducing stem cell self renewal in the absence of differentiation, as well as proteins having additional biological functions; (vi) isolation of 3D stromal cell RNA for cloning of novel stromal cell-associated stem cell regulators and additional functional stromal cell gene products.

Figure 1:
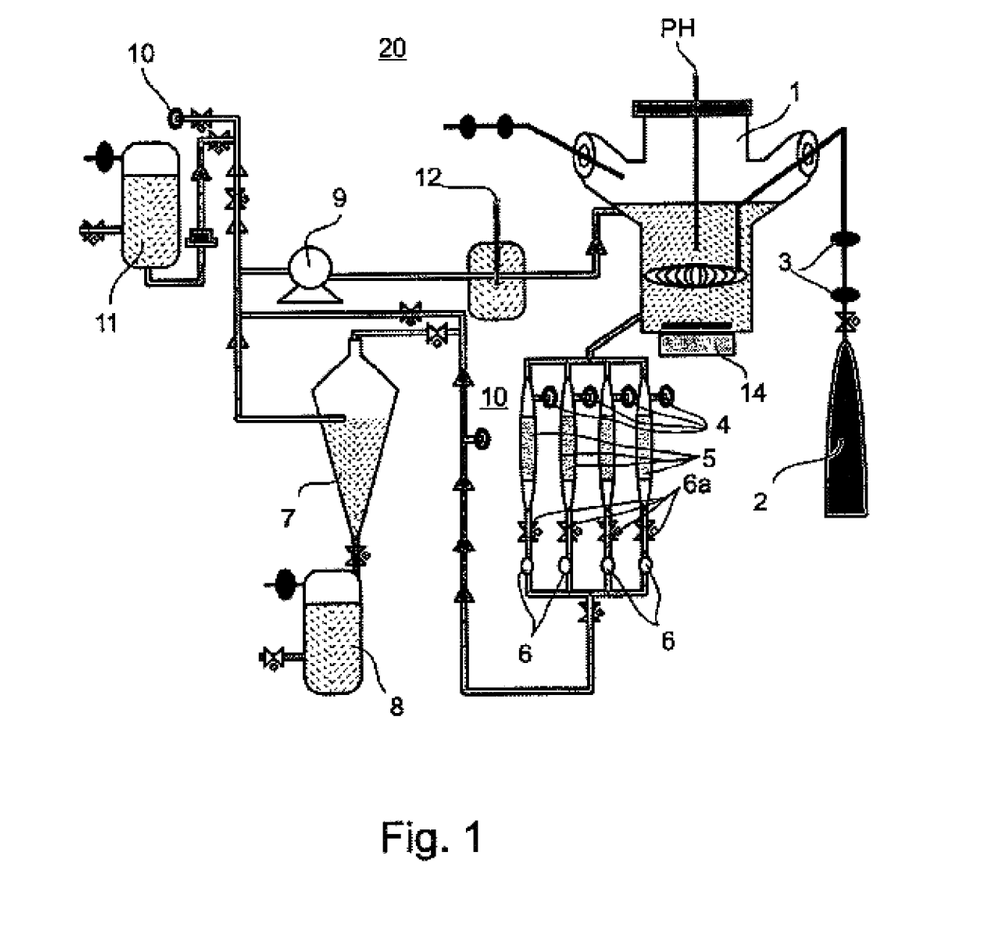
FIG. 1 is a schematic depiction of an exemplary plug-flow bioreactor 20 which served while reducing the present invention to practice; 1—medium reservoir; 2—gas mixture container; 3—gas filters; 4—injection points; 5—plug or container of plug flow bioreactor 20; 6—flow monitors; 6a—flow valves; 7—conditioned medium collecting/separating container; 8—container for medium exchange; 9—peristaltic pump; 10—sampling point; 11—container for medium exchange; 12—$O_2$ monitor; 14—steering device; PH—pH probe.

According to one aspect of the present invention there is provided a method of expanding/maintaining undifferentiated hemopoietic stem cells or progenitor cells. The method according to this aspect of the present invention is effected by implementing the following method steps. First, undifferentiated hemopoietic stem cells or progenitor cells are obtained. Second, the undifferentiated hemopoietic stem cells or progenitor cells are seeded into a stationary phase plug-flow bioreactor, an example of which is depicted in FIG. 1 along with reference numerals, in which a three dimensional stromal cell culture, of either stromal cell line or primary stromal cell culture, have been pre-established on a substrate in the form of a sheet, the substrate including a non-woven fibrous matrix forming a physiologically acceptable three-dimensional network of fibers, thereby, as is further described above and exemplified in the Examples section that follows, expanding/maintaining undifferentiated hemopoietic stem cells or progenitor cells.

As used herein in the specification and in the claims section that follows, the phrase "undifferentiated hemopoietic stem cells" refers to uncommitted hemopoietic cells.

As used herein in the specification and in the claims section that follows, the phrase "progenitor cells" refers to committed, yet immature hemopoietic cells.

Both undifferentiated hemopoietic stem cells and progenitor cells are CD34+ cells. Thus, the phrase "obtaining undifferentiated hemopoietic stem cells or progenitor cells" and its equivalent phrase "undifferentiated hemopoietic stem cells or progenitor cells are obtained" both refer to the obtainment of either isolated undifferentiated hemopoietic stem cells and/or progenitor cells, or a population of CD34+ cells which contain undifferentiated hemopoietic stem cells and progenitor cells.

As used herein in the specification and in the claims section that follows, the terms "expanding" and "expansion" refer to substantially differentiationless cell growth, i.e., increase of a cell population without differentiation accompanying such increase.

As used herein in the specification and in the claims section that follows, the terms "maintaining" and "maintenance" refer to substantially differentiationless cell renewal, i.e., substantially stationary cell population without differentiation accompanying such stationarity.

As used herein the term "differentiation" refers to change from relatively generalized to specialized kinds during development. Cell differentiation of various cell lineages is a well documented process and requires no further description herein.

As used herein the term "ex-vivo" refers to cells removed from a living organism and are propagated outside the organism (e.g., in a test tube).

Following expansion, for example, the now expanded undifferentiated hemopoietic stem cells or progenitor cells can be isolated by a variety of affinity separation/labeling techniques, such as, but not limited to, fluorescence activated cell sorting and affinity separation via an affinity substrate. Affinity molecules which can be used to implement such isolation methods include anti-CD34 antibodies, for example, which bind CD34+ cells.

According to another aspect of the present invention there is provided another method of expanding/maintaining undifferentiated hemopoietic stem cells or progenitor cells. The method according to this aspect of the present invention is effected by implementing. the following method steps. First, undifferentiated hemopoietic stem cells or progenitor cells are obtained. Second, the undifferentiated hemopoietic stem cells or progenitor cells are cultured in a medium containing, as a sole ingredient or as an additive, a stromal cell conditioned medium, the stromal cell conditioned medium being derived from a stationary phase plug-flow bioreactor in which a three dimensional stromal cell culture, of either stromal cell line or primary stromal cell culture, have been established on a substrate in the form of a sheet, the substrate including a non-woven fibrous matrix forming a physiologically acceptable three-dimensional network of fibers, thereby, as is further described above and exemplified in the Examples section that follows, expanding/maintaining undifferentiated hemopoietic stem cells or progenitor cells.

According to yet another aspect of the present invention there is provided a method of preparing a stromal cell conditioned medium useful in expanding/maintaining undifferentiated hemopoietic stem cells or progenitor cells. The method according to this aspect of the present invention is effected by implementing the following method steps. First, a stromal cell culture, of either stromal cell line or primary stromal cell culture, is established in a stationary phase plug-flow bioreactor on a substrate in the form of a sheet, the substrate including a non-woven fibrous matrix forming a physiologically acceptable three-dimensional network of fibers, thereby expanding/maintaining undifferentiated hemopoietic stem cells or progenitor cells. second, when a desired stromal cell density has been achieved, say, for example, above $5 \times 10^6$ or above $10^7$ cells per cubic centimeter of the matrix, collecting medium from the stationary phase plug-flow bioreactor, as is further described above and exemplified in the Examples section that follows, obtaining the stromal cell conditioned medium useful in expanding/maintaining undifferentiated hemopoietic stem cells or progenitor cells.

According to still another aspect of the present invention there is provided a method of transplanting undifferentiated hemopoietic stein cells or progenitor cells into a recipient. The method according to this aspect of the present invention is effected by implementing the following is method steps. First, the undifferentiated hemopoietic stem cells or progenitor cells are expanded/maintained by any of the methods described above. Second, the undifferentiated hemopoietic stem cells or progenitor cells resulting from the first step are transplanted in the recipient.

As is shown in FIG. 1, according to yet an additional aspect of the present invention there is provided a bioreactor plug comprising a container 5, typically in the form of a column, having an outlet and an inlet and containing therein a substrate in the form of a sheet, the substrate including a non-woven fibrous matrix forming a physiologically acceptable three-dimensional network of fibers, the substrate supporting at least $5 \times 10^6$ stromal cells, preferably, at least $10^7$, of either stromal cell line or primary stromal cell culture, per cubic centimeter of the substrate.

According to still an additional aspect of the present invention there is provided a plug-flow bioreactor comprising the above bioreactor plug.

It will be appreciated in this respect that the substrate may theoretically support up to $5 \times 10^7$ cells per cubic centimeter thereof. Once sufficient cells have accumulated on the substrate, means such as irradiation can be employed to cease further cell growth, so as to control the exact number of cells supported by the substrate.

The undifferentiated hemopoietic stem cells or progenitor cells which are used as a source for such cells while implementing the methods of the present invention can be purified or isolated from a tissue, such as, but not limited to, cord blood, cytokine-mobilized peripheral blood (collected by, for example, leukapheresis) and bone-marrow, all of which are known to include undifferentiated hemopoietic stem cells or progenitor cells. Methods of such separation are well known in the art, the most frequently used being fluorescence activated cell sorting in which cells are first tagged by affinity labeling with a fluorophore and are than collected.

According to a preferred embodiment of the present invention the undifferentiated hemopoietic stem cells or progenitor cells and stromal cells of the stromal cell culture share common HLA antigens. According to another preferred embodiment of the present invention the undifferentiated hemopoietic stem cells or progenitor cells and the stromal cells of the stromal cell culture are from a single individual. Thus, separation of cells is not required in case of transplantation thereof to a recipient.

According to still another preferred embodiment of the present invention the undifferentiated hemopoietic stem cells or progenitor cells and stromal cells of the stromal cell culture are from different individuals. For example, a future recipient of the undifferentiated hemopoietic stem cells or progenitor cells and stromal cells be used to provide the stromal cells, whereas the undifferentiated hemopoietic stem cells or progenitor cells and stromal cells are from a donor selected according to HLA compatibility to donate such cells to the recipient. Thus, again, separation of cells is not required prior to transplantation.

According to another embodiment of the present invention the undifferentiated hemopoietic stem cells or progenitor cells and stromal cells of the stromal cell culture are from the same species. However, according to still another preferred embodiment of the present invention the undifferentiated hemopoietic stem cells or progenitor cells and stromal cells of the stromal cell culture are from different species.

According to a presently preferred embodiment of the present invention the step of seeding the undifferentiated hemopoietic stem cells or progenitor cells into the stationary phase plug-flow bioreactor is effected while flow in the bioreactor is shut off for at least 10 hours following such seeding, so as to enable the cells to anchor to the stromal cell covered matrix.

The following descriptions provide insight with respect to preferred substrates which are used while implementing the present invention.

Thus, according to one embodiment the fibers of the substrate form a pore volume as a percentage of total volume of from 40 to 95% and a pore size of from 10 microns to 100 microns. According to another embodiment, the matrix making the substrate is made of fiber selected from the group consisting of flat, non-round, and hollow fibers and mixtures thereof, the fibers being of from 0.5 microns to 50 microns in diameter or width. According to still another embodiment, the matrix is composed of ribbon formed fibers having a width of from 2 microns. According to a further embodiment, the ratio of width to thickness of the fibers is at least 2:1. According to still a further embodiment, the matrix making the substrate having a pore volume as a percentage of total volume of from 60 to 95%. According to still another embodiment, the matrix has a height of 50–1000 μm, whereas stacks thereof are employed. According to yet another embodiment, the material of the matrix making the substrate is selected from the group consisting of polyesters, polyalkylenes, polyfluorochloroethylenes, polyvinyl chloride, polystyrene, polysulfones. cellulose acetate, glass fibers, and inert metal fibers. According to still another embodiment, the matrix is in a shape selected from the group consisting of squares, rings, discs, and cruciforms. According to still another embodiment, the matrix is coated with poly-D-lysine.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature, See, for example, "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I–III Cellis, J. E., ed. (1994); "Current Protocols in Immunology" Volumes I–III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S J., eds. (1984); "Animal Cell s Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Methods

Bioreactor: The bioreactor used in accordance with the teachings of the present invention was constructed in accordance with the design described in FIG. 1. The glassware was designed and manufactured at the Technion (Israel) and connected by silicone tubing (Degania, Israel). The carriers were rotated overnight in phosphate buffered saline (PBS; Beit Ha'Emek Industries, Israel) without $Ca^{+2}$ and $Mg^{+2}$, followed by removal of the PBS and released debris. Each column was loaded with 10 ml packed carrier. The bioreactor was filled with PBS-Ca-Mg, all outlets were sealed and the system was autoclaved (120° C., 30 minutes). The PBS was removed via container [8] and the bioreactor was circulated in a 37° C. incubator with 300 ml Dulbecco's high-glucose medium (DMEM; GIBCO BRL) containing 10% heat-inactivated fetal calf serum (FCS; Beit Ha'Emek Industries, Israel) and a Pen-Strep-Nystatin mixture (100 U/ml:100 μg/ml:1.25 μn/ml; Beit Ha'Emek), for a period of 48 hours. Circulating medium was replaced with fresh DMEM containing the above +2 mM L-glutamine (Beit Ha'Emek).

Stromal cells: Stromal cell lines were maintained at 37° C. in DMEM supplemented with 10% FCS, in a fully humidified incubator of 5% $CO_2$ in air. Cells were grown in tissue culture flasks (Coming) and were split by trypsinization upon reaching confluence. Primary human marrow stromal cultures were established from aspirated sternal marrow of hematologically healthy donors undergoing open-heart surgery. Briefly, marrow aspirates were diluted 3-fold in Hank's Balanced Salts Solution (HBSS; GIBCO BRL) and were subject to Ficoll-Hypaque (Robbins Scientific Corp. Sunnyvale, Calif.) density gradient centrifugation. Marrow mononuclear cells (<1.077 gm/cm$^3$) were collected, washed 3 times in HBSS and resuspended in long-term culture (LTC) medium, consisting of DMEM supplemented with 12.5% FCS, 12.5% horse serum (Beit Ha'Emek), 10$^{-4}$ M β-mercaptoethanol (Merck) and 10–6 mol/L hydrocortwasone sodium succinate (Sigma). Cells were incubated in 25 ml tissue culture flasks (Corning) for 3 days at 37° C. (5% CO$_2$) and then at 33° C. (idem) with weekly culture refeeding. Stromal cells from individual donors were employed for each bioreactor. For 3D and monolayer studies, primary stromal cell cultures were split by trypsinization (0.25% Trypsin and EDTA in Puck's Saline A; Beit Ha'Emek) every 10 days, to allow sufficient stromal cell expansion. For LTC-IC and CAFC (see below), stromal cells were irradiated (1500 coy) using a $^{137}$Cs source, cultures were maintained at 33° C. in LTC medium.

Seeding of stromal cells: Confluent cultures of stromal cell lines or 5-week primary marrow stromal cells were trypsinized and the cells washed 3 times in HBSS, resuspended in bioreactor medium (see above), counted and seeded at 10$^6$ cells/ml in 10 ml volumes via an injection point ([4], FIG. 1) onto 10 ml carriers in the glass column of the bioreactor. Immediately following seeding, circulation was stopped for 16 hours to allow the cells to settle on the carriers. Stromal cell growth in the bioreactor was monitored by removal of carriers and cell enumeration by the MT method (56). When stromal cells were confluent, medium was replaced with LTC medium, for continued studies (preparation of SCM, stem cell seeding).

Preparation of stromal cell conditioned medium (SCM): At equivalent cell densities, monolayer and bioreactor stromal cells were recharged with fresh LTC culture medium. SCM was collected following overnight incubation of the cells. For this purpose, medium flow in the 3D cultures was stopped for 16 hours and removed directly from the column prior to re-initiation of circulation. For analysis of the effect of CD34+ cells on stromal cell production of SRC, circulation was stopped at various intervals (2–7 days) after seeding of CD34+into the 3D system and medium collected from the column as described above. SCM was spun (1000× g, 10 minutes), filtered and stored at −20° C. Stromal cells were also grown in the bioreactor in serum-free medium, for the collection of SCM, thereby excluding undefined variables.

Isolation of CD34+ cells: Umbilical cord blood samples taken under sterile conditions during delivery were fractionated on Ficoll-Hypaque and buoyant (<1.077 gr/cm$^3$) mononuclear cells collected. Cells from individual CB samples were pooled, incubated with anti-CD34 antibodies and isolated by midi MACS (Miltenyl Biotech).

Suspension cultures of CD34+ cells: CB CD34+ cells (5×10$^5$/well) were incubated in 24-well dishes (TPP, Switzerland), in 0.5 ml of 0–100 % SCM, minus or plus 300 ng/ml each of FLT3 ligand, SCF, or TPO, alone or combined. Controls contained LTC medium plus or minus cytokines. Cells were incubated at 37° C. at 5% CO$_2$ in air. Culture medium was exchanged weekly. Prior to seeding and at various times (1–3 weeks), cells were harvested, enumerated and assayed for CD34+/38−/CXCR4+by flow cytometry. Output assays can also include SRC, CAFC and LTC-IC.

Stromal-stem cell cocultures: Isolated, pooled CB CD34+ cells were seeded at equivalent numbers (about 5×10$^5$) onto monolayer or bioreactor containing equivalent densities of confluent stromal cells. Upon addition to the bioreactor, medium flow was stopped for 16 hours to enable contact with stromal cells and was re-initiated at a rate of 0.1–1.0 ml per minute. CD34+ cell seeded-stromal cell carriers were removed for control studies in the absence of medium exchange. Cocultures were maintained in LTC medium, with or without cytokines. At various times (up to 4 weeks), nonadherent cells were collected from monolayer supernatants or from circulating culture medium via a container ([8], FIG. 1). Adherent cells were collected via sequential trypsinization and exposure to EDTA-based dissociation buffer (GIBCO BRL), followed by gentle pipetting of the cells. To avoid the presence of stromal cells in the resulting suspension, the cells were resuspended in HBSS +10% FCS and were subjected to a 60 minutes adhesion procedure in plastic tissue culture dishes (Corning), at 37° C. Circulating and carrier-isolated hemopoietic cells were washed, counted and assayed separately for CD34+/38−/CXCR4+ by flow cytometry. Output assays can also include SRC, CAFC and LTC-IC.

Flow Cytometry: Cells were incubated at 4° C. for 30 minutes with saturating concentrations of monoclonal anti-CD34+PerCP (Beckton-Dickinson), anti-CXCR4-fluorescein isothiocyanate (FITC, R&D systems) and—phycoerythrin (PE, Beckton-Dickinson) antibodies. The cells were washed twice in ice-cold PBS containing 5% heat-inactivated FCS and resuspended for three-color flow cytometry on a FACSscan (Beckton-Dickinson).

LTC-IC and CAFC assays: Freshly isolated CD34+ cells, cells isolated from stromal-stem cell cocultures or from suspension cultures, were assayed for LTC-IC and CAFC, as previously described (16, 17). Confluent primary marrow stromal cells were trypsinized, irradiated (1500 cGy) and plated in 0.1 ml in 96-well dishes (Corning) at 1.5×10$^4$/well. 24 replicate wells/group were established. Stromal cells were overlaid with 0.1 ml of LTC medium containing serial dilutions of CD34+ cells (500–5 cells/well), or with serial dilutions of cells harvested from various assays. Cultures were directly incubated at 33° C. for 5 weeks, with weekly half-medium exchange. Plates were spun down at 1000 rpm for 10 minutes, culture supernatants removed and remaining cells overlayed with methylcellulose cultures and cytokines for myeloid progenitor cell assays, as previously described (57). Colonies were enumerated following 14 days and LTC-IC frequency determined according to the reciprocal of the concentration of test cells that gives 37% negative cultures (16). The CAFC assay was basically performed as above except for the absence of overlay of methylcellulose and cytokines. The percentage of wells with at least one phase-dark hemopoietic clone of at least five cells (cobblestone area) beneath the stromal layer was determined at week 6 following seeding of the test cell suspensions, in serial dilutions.

Experimental Results

The bioreactor system employed while reducing the present invention to practice is depicted in FIG. 1. It contained four parallel plug flow bioreactor units[5]. Each bioreactor unit contained 1 gram of porrosive carriers (4 mm in diameter) made of a non woven fabric matrix of polyester (58). These carriers enable the propagation of large cell numbers in a relatively small volume. The structure and packing of the carrier have a major impact on oxygen and nutrient transfer, as well as on local concentrations and released stromal cell products (e.g., ECM proteins, cytokines, 59). The bioreactor was maintained in an incubator of 37° C.

The flow in each bioreactor was monitored and [6] regulated by a valve[6a]. Each bioreactor contains a sampling and injection point [4], allowing the sequential seeding of stromal and hemopoietic cells. Culture medium was supplied at pH 7.0 [13] from a reservoir [1]. The reservoir was supplied by a filtered [3] gas mixture containing air/$CO_2O_2$ [2] at differing proportions in order to maintain 5–40% dissolved oxygen at exit from the column, depending on cell density in the bioreactor. The $O_2$ proportion was suited to the level of dissolved $O_2$ at the bioreactor exit, as was determined by a monitor [12]. The gas mixture was supplied to the reservoir via silicone tubes. The culture medium was passed through a separating container [7] which enabled collection of circulating, nonadherent cells. Circulation of the medium was obtained by means of a peristaltic pump [9] operating at a rate of 0.1–3 ml/minute. The bioreactor units were equipped with an additional sampling point [10] and two containers [8, 11] for continuous medium exchange at a rate of 10–50 ml/day. The use of four parallel bioreactor units enables periodic dismantling for purposes such as cell removal, scanning electron microscopy, histology, immunohistochemistry, RNA extraction, etc.

Figure 2:
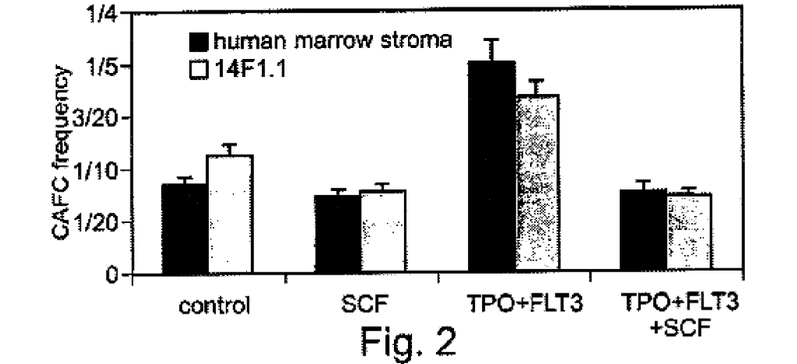
FIG. 2 demonstrates CAFC maintenance by 14F1.1 cells. Cord blood CD34+ cells were seeded at limiting dilution onto irradiated 14F1.1 or primary human marrow stroma. Cobblestone formation was determined 5 weeks later. Results represent the mean ±SD of 2 independent experiments.
Figure 3:
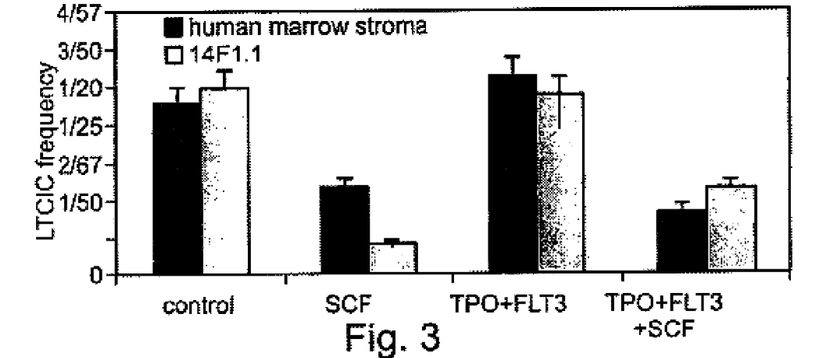
FIG. 3 demonstrates LTC-IC maintenance by 14F1.1 cells. Cord blood CD34+ cells were seeded at limiting dilution onto irradiated 14F1.1 or primary human marrow stroma. Myeloid colony formation was determined 7 weeks later. FLT-3 ligand (300 ng/ml), TPO (300 ng/ml) and SCF (100 ng/ml) were added with weekly medium replacement. Results represent the mean ±SD of 2 experiments.
Figure 4:
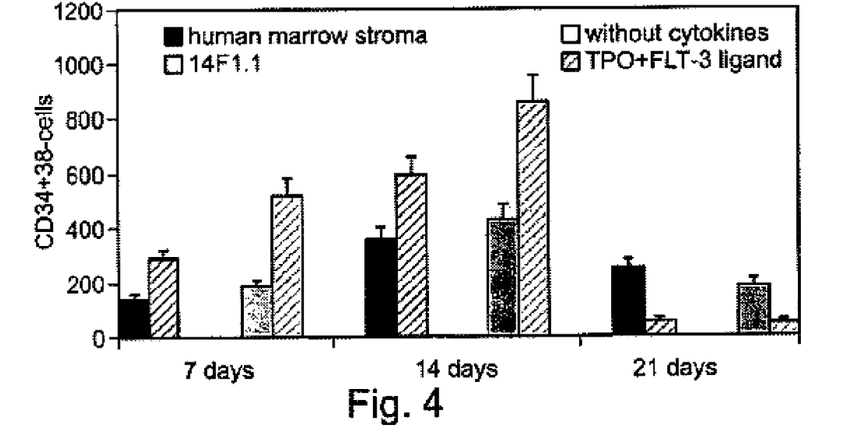
FIG. 4 demonstrates expansion of CD34+38− cells on 14F1.1 and primary human marrow stroma. CD34+ cells were seeded onto 14F1.1 or human marrow stroma at 70 CD34+38− cells/well. Cytokines were added weekly. Cultures were trypsinized 7–21 days later. CD34+38− were determined by FACS analysis. Results represent the mean ±SD of 2 independent experiments.
Figure 5A:
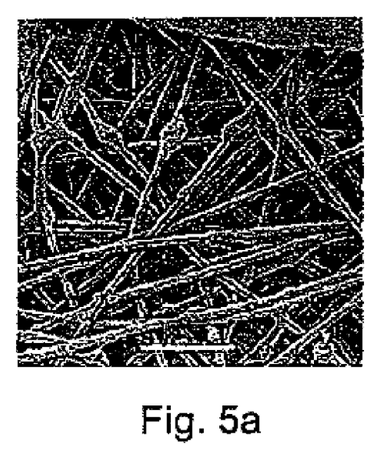
FIGS. 5a–b show scanning electron micrographs (SEM) of carrier seeded with 14F1.1 stromal cell line following 10 days (FIG. 5a) or following 40 days (Figure b). Magnification: ×150.
Figure 5B:
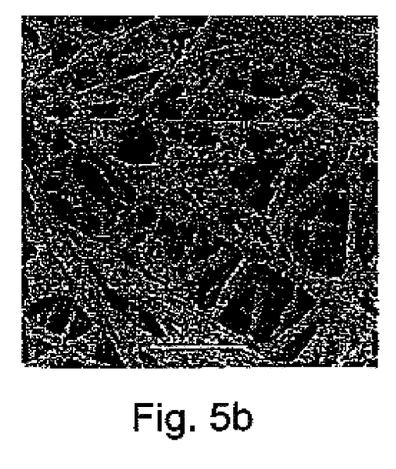

In one experiment a bioreactor system containing the murine 14F1.1 stromal cell line (24, 60, 61), which was previously shown to support the growth of committed human myeloid progenitors (24) has been established. This cell line can also equally support human CB CAFC (FIG. 2), LTC-IC (FIG. 3) and CD34+38− cells (FIG. 4), as well as primary human marrow stromal cells. The results presented in these Figures also show that the addition of FLT3 ligand+ TPO to these cultures has no effect on LTC-IC, whereas these cytokines significantly enhanced CAFC and CD34+ 38− cell output. In contrast, SCF induced a decline in both LTC-IC and CAFC. When seeded into the bioreactor at $1.5 \times 10^6$ cells/10 ml culture volume, 14F1.1 cells grew and spread on the carriers (FIG. 5). By day 40 following seeding, the carriers contained a 100-fold increased cell density, i.e., approximately $1.5 \times 10^6$ cells/carrier, $1.5 \times 10^7$ cells/ml (Table 1).

The cellular density on carriers at various levels of the column was the same, indicating a homogenous transfer of oxygen and nutrients to the cells. The culture conditions were optimized for these cells: culture medium (Dulbecco's high-glucose medium +10% fetal calf serum), flow rate (1 ml/min), medium exchange frequency (once a week), initial seeding density (as above). No beneficial effect was found for collagen or poly L-lysine carrier coating, on the growth rate and final density of 14F1.1 cells. Preliminary findings with primary human marrow stromal cells (Table I) indicated a similar density of 1 4F1.1 and primary stromal cells, on days 10 and 14 following seeding, respectively.

In order to assay the functional activity of the stromal cells within the bioreactor, the effect of stromal cells conditioned medium (SCM) obtained from the bioreactor column (3D SCM), on the expansion of CD34+38− cells in suspension cultures seeded with human CB CD34+ cells was determined. The activity was compared to SCM obtained from monolayer cultures (2D SCM) containing the same concentration of stromal cells. As shown in FIG. 6, SCM from 14F1.1 cells was found to be equally or more capable of supporting the maintenance of human CB CD34+ 38− cells, than SCM from primary marrow stromal cells. A maximal effect of 14F1.1 SCM was consistently observed at a lower concentration than that of primary marrow SCM. Furthermore, 3D SCM was found to be superior to 2D SCM of both cell types, in supporting the expansion of human CB CD34+38− cells. The difference in activity between 2D and 3D SCM was more pronounced with culture duration (14 versus 21 days). The addition of 14F1.1 3D SCM to suspension cultures of human CB CD34+ cells also resulted in the maintenance of CD34+38−CXCR4+ cells (Table 2), as compared to control cultures containing medium alone.

TABLE 2

Effect of 3D 4F1.1 SCM on yield of CD34+38−/CD34+38−CXCR4+

| Cell surface phenotype | LTC medium | 14F1.1 SCM (50%) |
|---|---|---|
| CD34+38− | 370 | 1296 |
| CD34+38−CXCR4+ | 0 | 38 |

Human CB CD34+ cells ($8 \times 10^4$/point) were seeded in suspension cultures containing LTC medium or 50% 3D 14F1.1 SCM. Cultures were harvested 7 days later and cells analyzed by FACS. CD34+38− and CD34+38−CXCR4+ inputs were 2800 and 112, respectively.

TABLE 1

Kinetics of 14F1.1 and primary human marrow stroma growth on carriers

| | Time of stromal on carrier (days) | | | | |
|---|---|---|---|---|---|
| | 10 14F1.1 | 14 human stroma | 20 14F1.1 | 30 14F1.1 | 40 14F1.1 |
| Top part | $1.5 \times 10^3$ | $1.5 \times 10^3$ | $1 \times 10^5$ | $3.5 \times 10^5$ | $1.3 \times 10^6$ |
| Middle part | $1 \times 10^3$ | $1.2 \times 10^3$ | $1.3 \times 10^5$ | $2.0 \times 10^5$ | $1.3 \times 10^6$ |
| Bottom part | $1 \times 10^3$ | $1 \times 10^3$ | $7 \times 10^4$ | $2.0 \times 10^5$ | $1.5 \times 10^6$ |

MTT analysis included 5 carriers/determination. Mean of 2 independent experiments.

Table 3 demonstrates the effect of cytokines in suspension cultures of CD34+ containing 2D versus 3D SCM. The results clearly demonstrate that 3D SCM was superior to 2D SCM in supporting the maintenance of both CD34+38− and more importantly, the CD34+38−CXCR4+ (SRC) subset.

TABLE 3

Effect of cytokines on expansion of CD34+38−/CD34+38−CXCR4+ cells in 3D 14F1.1 SCM

| Cell surface phenotype | 2D 14F1.1 SCM (50%) | | | 3D 14F1.1 SCM (50%) | | |
|---|---|---|---|---|---|---|
| | alone | FLT$_3$ ligand + TPO | SCF | alone | FLT$_3$ ligand + TPO | SCF |
| CD34+38− | 1820 | 140 | 0 | 2720 | 4080 | 130 |
| CD34+38−CXCR4+ | 460 | 70 | 0 | 620 | 930 | 0 |
| CD34+ | 37,000 | 178,000 | 361,000 | 17,000 | 25,000 | 210,000 |

Human CB CD34+ cells (2.6 × 10$^5$/point) 50% 2D vs 3D 14F1.1 SCM, in the absence or presence of FLT3 ligand (300 ng/ml) TPO (300 ng/ml) or SCF (50 ng/ml). Cultures were harvested 7 days later and cells analyzed by FACS. CD34+38− and CD34+38−CXCR4+ inputs were 7900 and 360, respectively.

This may be related to the stronger effect of 2D SCM on cell differentiation, as detected by the yield of CD34+ cells. TPO+FLT$_3$ ligand reduced the yield of CD34+38−/CD34+ 38−CXCR4+ in the presence of 2D SCM but enhanced their yield in cultures supplemented with 3D SCM. Again, this can be attributed to the lesser extent of differentiation in the 3D system, as determined by the CD34+ surface marker. In both 2D and 3D SCM cultures, SCF induced a marked increase in stem cell differentiation and a marked decline in the yield of CD34+38−/CD34+38−CXCR4+ cells.

Figure 7:
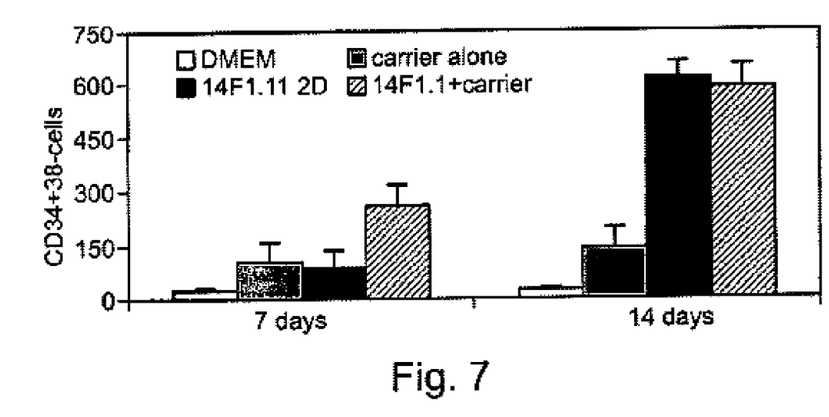
FIG. 7 demonstrates maintenance of CD34+38− cells on stromal-cell coated carriers. Stromal cell-coated carriers were removed from the 3D system into silicone-coated 96-well dishes, followed by addition of $1.5 \times 10^4$ CD34+ cells. Controls contained carriers alone and carrier-equivalent numbers of monolayer (2D) grown 14F1.1 cells. Cells were harvested at the designated times and analyzed by FACS. Results represent the mean ±SD of 2 independent experiments.

In order to assay stromal-stem cell interactions in our bioreactor, the maintenance/expansion of CD34+38− cells on stromal cell (14F1.1)-coated carriers was first evaluated. The latter were removed from the bioreactor into silicone-coated 96-well dishes, followed by the addition of CD34+ cells. Controls contained carriers alone and carrier-equivalent numbers of monolayer 14F1.1) cells. As shown in FIG. 7, the survival of CD34+38− cells was enhanced by the presence of the carrier alone, confirming the beneficial effect of a 3D structure on the survival/maintenance of primitive progenitors (36). Stromal-cell coated carriers were superior to carriers alone or to monolayer 14F1.1 cells, in promoting the 7-day survival/maintenance of CD34+38− cells. Prolonged culture (day 14) resulted in increased CD34+38− numbers in both 14F1.1 monolayer and 14F1.1 -coated carrier cultures.

In a subsequent experiment 6×10$^6$ pooled CB CD34+ (3×10$^5$ CD34+38−) cells were seeded into a bioreactor containing 4 columns of non-irradiated, 14F1.1 -coated carriers, in 350 ml circulating culture medium. Medium flow was stopped for 16 hours and continued thereafter at a normal rate (1 ml/min). Following 4 days of coculture, circulating medium contained 10% of the initially seeded CD34+38− cells, determined by FACS analysis of harvested viable cells. Following days of culture, circulating medium contained 0.4% CD34+38− cells, while carrier -adherent cells contained 3% of the initially seeded CD34+38− population.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety. Citation or identification of any reference in this application shall not be construed as an admission that such reference is available as prior art to the present invention.

References

1. Turhan, A. G., Humphries, R. K., Phillips, G. L., Eaves, A. C. & Eaves, C. J. N.Engl. J. Med. 320:1655, 1989.
2. Morrison, S. J., Uchida, N. & Weissman I. L. Ann. Rev. Cell. Dev. Biol. 11:35,1995.
3. Ogawa, M. Blood 11:2844,1993.
4. Lord B I, Testa N G, Hendry J H. Blood 45:65, 1995.
5. Trentin J J. in Gordon A (ed): Regulation of Hematopoiesis Vol I. New York, N.Y., Appleton-Century-Crafts, p161, 1970.
6. Wolf N S. Clin. Hematol. 8:469, 1979.
7. Dorshkind K, Ann. Rev. Immunol. 8:11, 1990.
8. Allen T D, Dexter T M. Exp. Hematol. 12;517, 1984.
9. Gupta P, McCarthy J B, Verfaillie C M. Blood 87:3229, 1996.
10. Liesveld J L, Winslow J M, Kempshi M C, Ryan D H, Brennan J K, Abboud C N. Exp. Hematol. 19:63, 1991.
11. Long M W, Briddel R, Walter A W, Bruno E, Hoffman R. J. Clin. Invest. 90:251, 1992.
12. Eaves C J, Cashman J D, Kay R J, Daugherty G J, Otsuka T, Gabury L A, Hogge DE, Landsdorp P M, Eaves A C, Humphries R K. Blood 78:110, 1991.
13. Moore K A, Pytowski B, Witte L, Hicklin D, Lemischka I. Proc. Nat. Acad. Sci. 94:4011, 1997.
14. Li L, Milner L A, Deng Y, Iwata M, Banta A, Graf L, Marcovina S, Friedman C, Trask B J, Hood L, Torok-Storb B. Immunity 8:43, 1998.
15. Allen T D, Dexter T M. Exp. Hematol. 12;517,1984.
16. Sutherland H, Landsdorp P M, Henkelman D, Eaves A C, Eaves C J. Proc. Nat. Acad. Sci. 87:3584, 1990
17. Breems D A, Blokland E A W, Nben S, Ploemacher R E. Leukemia 8:1095, 1994.
18. Verfaillie C, Blakolmer K, McGlare P. J. Exp. Med. 172:509, 1990.
19. Burroughs J, Gupta P, Blazar B, Verfaillie C. Exp. Hematol. 22:1095, 1994.
20. Roecklein BA, Torok-Storb B. Blood 85: 997, 1995.
21. Thiemann F T, Moore K A, Smogorzewska E M, Lemischka I R, Crooks G M. Exp. Hematol. 26:612, 1998.

22. Breems D A, Blokland E A W, Siebel K E, Mayen A E M, Engels L J A, Ploemacher R E. Blood 91:111, 1998.
23. Aiuti A, Friedrich C, Sieff C A, Gutierrez-Ramos J C. Exp. Hematol. 26:143, 1998.
24. Otsuka T, Satoh H, Ogo T, Bairy O, Gluck U, Zipori D, Nakano T, Okamura Y, Niho Y. Int. J. Cell Cloning 10:153, 1992.
25. Larochelle A, Vormoor J, Hahenberg H, Wang J C Y, Bhatia M, Lapidot T, Moritz T, Murdoch B, Xiao L X, Kato I, Willimas D A & Dick J E. Nat. Med. 2:1329,1996.
26. Gan OI, Murdoch B, Larochelle A, Dick J E. Blood 90:641, 1997.
27. Shultz L D, Schweitzer A, Christianson S W, Gott B, Shweitzer I B, Tennent B, McKenna S, Mobraaten L, Rajan T V, Greiner D L, Leiter E H. J. Immunol. 154:180, 1995.
28. Larochelle A, Vormoor J, Lapidot T, Sher G, Furukawa T, :I Q, Shultz L, Oliveri N F, Stamatoyannoppoulus G & Dick J E. Hum. Mol. Genet. 4:163, 1995.
29. Larochelle A, Vormoor J, Hahenberg H, Wang J C Y. Bhatia M, Lapidot T, Moritz T, Murdoch B, Xiao L X, Kato I, Willimas D A & Dick J E. Nat. Med. 2:1329,1996.
30. Dick J E. Sem. Immunol. 8:197, 1996.
31. Bhatia M, Wang I C Y, Kapp U, Bonnet D, Dick J E. Proc. Natl. Acad. Sci. 94:5320, 1997.
32. Wang J C Y, Doedens M, Dick J E. Blood 89: 3919, 1997.
33. Peled A, Petit I, Kollet O, Magid M, Ponomaryov T, Nagler A, Ben-Hur H, Shultz L, Lider O, Alon R, Zipori D, Lapidot T. Science 283: 845–8. 1999
34. Bleul C C, Farzan M, Choe H, Parolin C, Clark-Lewis I, Legler D F, Loetscher M, Baggiolini M, Moser B. Nature 382:833, 1966.
35. Mizuno S, Wang J, Greenberger J, Glowacki J. Blood 88:189a (abs), 1996.
36. Rozenzweig M, Pykett M, Marks D F, Johnson R P. Gene Therapy 4:928, 1997.
37. Arakawa-Hoyt, Thiemann F T, Dao M A, Barsky L, Crooks G M, Nolta J A. Blood 92:581a, 1998 (Abst).
38. Moore K A, Pytowski B, Witte L, Hicklin D, Lemischka I. Proc. Nat. Acad. Sci. 94:4011, 1997.
39. Varnum-Finney B, Purton L E, Yu M, Brashem-Stein C, Flowers D, Staats S, Moore K A, Le Roux I, Mann R, Gray G, Artavanis-Tsakonas S, Bernstein I D. Blood 91:4084, 1998.
40. Verfaillie C M. Blood 79:2821, 1992.
41. Verfaillie C M. Blood 82:2045, 1993.
42. Bhatia R, McGlave P B, Miller J S, Wissink S, Lin W N, Verfaillie C M. Exp. Hematol. 25:980,1997.
43. Breems D A, Blokland E A W, Ploemacher R E. Leukemia 11:142, 1997.
44. Herman P H, Ferrant A, De Bruyere M, Straetmans N. Leukemia 12:735, 1998.
45. Breenis D A, Van Driel E M, Hawley R G, Siebel K E, Ploemacher R E. Leukemia 12:951, 1998.
46. Aiuti A, Ficara F, Dando J, Z E, Bordignon C. Blood 92:145a, 1998 (Abs).
47. Kusadasi N, van Soest P L, Ploemacher R E. Exp. Hematol. 25:699, 1998 (Abst).
48. Dorrell C, Gan O I, Pereira D S, Dick J E. Exp. Hematol. 25:688. 1998 (Abst).
49. Bhatia M, Bonnet D, Kapp U, Wang J C Y, Murdoch B, Dick J E. J. Exp. Med. 186:619,1997.
50. Kollet O, Moore J, Fajerman I, Ben-Hur H, Hagay Z, Nagler A, Feldman M, Lapidot T. Blood 90:365a, 1997 (Abs).
51. Bertolini F, Battaglia M, Lanza A, Palermo B, Soligo D, Robustelli della Cuna G. Blood 90:365a, 1997 (Abs).
52. Luens K M, Travis M A, Chen B P, Hill B L, Scollay R, Murray L J. Blood 91:1206, 1998.
53. Piacibello W, Sanavio F, Severino A, Dane A, Gammaitoni L, Fagioli F, Perissinotto E, Aglietta M. Blood. 93: 3736–49, 1999.
54. Kadouri A. Colloid and Surface B: Biointerface, 2:265, 1994.
55. Kadouri A, Kompier R, Honigwachs-Sha'anani J, Toledo J, Brosh N, Sternberg D, Levy A, Tzehoval E, Zipori D. Int. J. Cell Cloning 10:299, 1992.
56. Hansen M B, Nielsen S E, Berg K. J Immunol Methods 119:203, 1989.
57. Merchav S., Wagemaker G., Souza L. and Tatarsky I. Leukemia 5:344, 1991.
58. Kadouri A. Colloid and Surface B: Biointerface 2:265, 1994.
59. Kadouri A, Kompier R, Honigwachs-Sha'anani J, Toledo J, Brosh N, Stemberg D, Levy A, Tzehoval E, Zipori D. Int. J. Cell Cloning 10:299, 1992.
60. Zipori, D., Toledo, J. & von der Mark, K. Blood 66:447, 1985.
61. Otsuka T, Ogo T, Nakano t, Niiro H, Kuga S, Satoh H, Furukawa Y, Zipori D, Niho Y. Stem Cells 12:409, 1994.
62. Piacibello W, Sanavio F, Garetto L, Severino A, Bergandi D, Ferrario J, Fagioli F, Berger M, Aglietta M. Blood 89: 2644, 1997.
63. Carlo-Stella C, Mangoni L, Piovani G, Garau D. Almici C. Rizzoli V. Blood 83:1373, 1994.

What is claimed is:

1. A method of expanding undifferentiated hemopoietic stem cells to increase the number of the hemopoietic stem cells, the method comprising the steps of:
   (a) culturing in a stationary phase plug-flow bioreactor a stromal cell culture under continuous flow of a culture medium on a substrate in the form of a sheet, said substrate including a non-woven fibrous matrix forming a physiologically acceptable three-dimensional network of fibers to thereby generate a three dimensional stromal cell culture; and
   (b) seeding undifferentiated hemopoietic stem cells into said stationary phase plug-flow bioreactor including said three dimensional stromal cell culture and under said continuous flow of said culture medium, thereby expanding the undifferentiated hemopoietic stem cells to increase the number of the hemopoietic stem cells without the hemopoietic stem cells undergoing differentiation to obtain expanded undifferentiated hemopoietic stem cells.

2. The method of claim 1, wherein said undifferentiated hemopoietic stem cells are cells isolated from a tissue selected from the group consisting of cord blood, mobilized peripheral blood and bone-marrow.

3. The method of claim 1, wherein said undifferentiated hemopoietic stem cells and stromal cells of said stromal cell culture share common HLA antigens.

4. The method of claim 1, wherein said undifferentiated hemopoietic stem cells and stromal cells of said stromal cell culture are from a single individual.

5. The method of claim 1, wherein said undifferentiated hemopoietic stem cells and stromal cells of said stromal cell culture are from different individuals.

6. The method of claim 1, wherein said undifferentiated hemopoietic stem cells and stromal cells of said stromal cell culture are from the same species.

7. The method of claim 1, wherein said undifferentiated hemopoietic stem cells and stromal cells of said stromal cell culture are from different species.

8. The method of claim 1, wherein stromal cells of said stromal cell culture are grown to a density of at least $5\times10^6$ cells per a cubic centimeter of said substrate.

9. The method of claim 1, wherein stromal cells of said stromal cell culture are grown to a density of at least $10^7$ cells per a cubic centimeter of said substrate.

10. The method of claim 1, wherein said step of seeding said undifferentiated hemopoietic stem cells into said stationary phase plug-flow bioreactor is effected while flow in said bioreactor is shut off for at least 10 hours following said seeding.

11. The method of claim 1, wherein said fibers form a pore volume as a percentage of total volume of from 40 to 95% and a pore size of from 10 microns to 100 microns.

12. The method of claim 1, wherein said matrix is made of fiber selected from the group consisting of flat, non-round, and hollow fibers and mixtures thereof, said fibers being of from 0.5 microns to 50 microns in diameter or width.

13. The method of claim 1, wherein said matrix is composed of ribbon formed fibers having a width of from 2 microns to 20 microns, and wherein the ratio of width to thickness of the fibers is at least 2:1.

14. The method of claim 1, wherein said matrix having a pore volume as a percentage of total volume of from 60 to 95%.

15. The method of claim 1, wherein the matrix has a height of 50–1000 μm.

16. The method of claim 1, wherein the material of the matrix is selected from the group consisting of polyesters, polyalkylenes, polyfluorochloroethylenes, polyvinyl chloride, polystyrene, polysulfones, cellulose acetate, glass fibers, and inert metal fibers.

17. The method of claim 1, wherein the matrix is in a shape selected from the group consisting of squares, rings, discs, and cruciforms.

18. The method of claim 1, wherein the matrix is in the form of a disc.

19. The method of claim 1, wherein the matrix is coated with poly-D-lysine.

20. The method of claim 1, further comprising the step of isolating said undifferentiated hemopoietic stem cells.

21. A method of transplanting undifferentiated hemopoietic stem cells into a recipient, the method comprising the steps of:
 (a) expanding the undifferentiated hemopoietic stem cells to increase the number of the hemopoietic stem cells by:
  (i) culturing in a stationary phase plug-flow bioreactor a stromal cell culture under continuous flow of a culture medium on a substrate in the form of a sheet, said substrate including a non-woven fibrous matrix forming a physiologically acceptable three-dimensional network of fibers to thereby generate a three dimensional stromal cell culture; and
  (ii) seeding undifferentiated hemopoietic stem cells into said stationary phase plug-flow bioreactor including said three dimensional stromal cell culture and under a continuous flow of a culture medium, thereby expanding the undifferentiated hemopoietic stem cells increase the number of the hemopoietic stem cells without the hemopoietic stem cells undergoing differentiation to obtain expanded undifferentiated hemopoietic stem cells; and
 (b) transplanting the undifferentiated hemopoietic stem cells resulting from step (a) in the recipient.

22. The method of claim 21, wherein said undifferentiated hemopoietic stem cells are cells isolated from a tissue selected from the group consisting of cord blood, mobilized peripheral blood and bone-marrow.

23. The method of claim 21, wherein said undifferentiated hemopoietic stem cells and stromal cells of said stromal cell culture share common HLA antigens.

24. The method of claim 21, wherein said undifferentiated hemopoietic stem cells and stromal cells of said stromal cell culture are from a single individual.

25. The method of claim 21, wherein said undifferentiated hemopoietic stem cells and stromal cells of said stromal cell culture are from different individuals.

26. The method of claim 21, wherein said undifferentiated hemopoietic stem cells and stromal cells of said stromal cell culture are from the same species.

27. The method of claim 21, wherein said undifferentiated hemopoietic stem cells and stromal cells of said stromal cell culture are from different species.

28. The method of claim 21, wherein stromal cells of said stromal cell culture are grown to a density of at least $5\times10^6$ cells per a cubic centimeter of said substrate.

29. The method of claim 21, wherein stromal cells of said stromal cell culture are grown to a density of at least $10^7$ cells per a cubic centimeter of said substrate.

30. The method of claim 21, wherein said step of seeding said undifferentiated hemopoietic stem cells into said stationary phase plug-flow bioreactor is effected while flow in said bioreactor is shut off for at least 10 hours following said seeding.

31. The method of claim 21, wherein said fibers form a pore volume as a percentage of total volume of from 40 to 95% and a pore size of from 10 microns to 100 microns.

32. The method of claim 21, wherein said matrix is made of fiber selected from the group consisting of flat, non-round, and hollow fibers and mixtures thereof, said fibers being of from 0.5 microns to 50 microns in diameter or width.

33. The method of claim 21, wherein said matrix is composed of ribbon formed fibers having a width of from 2 microns to 20 microns, and wherein the ratio of width to thickness of the fibers is at least 2:1.

34. The method of claim 21, wherein said matrix having a pore volume as a percentage of total volume of from 60 to 95%.

35. The method of claim 21, wherein the matrix has a height of 50–1000 μm.

36. The method of claim 21, wherein the material of the matrix is selected from the group consisting of polyesters, polyalkylenes, polyfluorochloroethylenes, polyvinyl chloride, polystyrene, polysulfones, cellulose acetate, glass fibers, and inert metal fibers.

37. The method of claim 21, wherein the matrix is in a shape selected from the group consisting of squares, rings, discs, and cruciforms.

38. The method of claim 21, wherein the matrix is in the form of a disc.

39. The method of claim 21, wherein the matrix is coated with poly-D-lysine.

40. The method of claim 21, further comprising the step of isolating said undifferentiated hemopoietic stem cells prior to step (b).

* * * * *